United States Patent [19]

Alperin et al.

[11] 3,951,589

[45] Apr. 20, 1976

[54] AQUEOUS ALKALINE HAIR DYE COMPOSITIONS

[75] Inventors: George Alperin; Raymond Feinland, both of Stamford; Winfield H. Howard, Weston, all of Conn.

[73] Assignee: Clairol Incorporated, New York, N.Y.

[22] Filed: Feb. 21, 1975

[21] Appl. No.: 551,890

Related U.S. Application Data

[63] Continuation of Ser. No. 309,498, Nov. 24, 1972, abandoned.

[52] U.S. Cl. .................................................. 8/10.1
[51] Int. Cl.² ......................................... A61K 7/12
[58] Field of Search ...................................... 8/10.1

[56] References Cited
UNITED STATES PATENTS

| | | | |
|---|---|---|---|
| 2,750,327 | 6/1956 | Eckardt et al. | 8/10.1 |
| 3,168,442 | 2/1965 | Brunner et al. | 8/10.1 |

*Primary Examiner*—Leonard Schenkman
*Attorney, Agent, or Firm*—Irving Holtzman; George A. Mentis; David J. Mugford

[57] ABSTRACT

An aqueous alkaline hair dye composition containing N¹,N⁴,N⁴-tris(2′-hydroxyethyl)-2-nitro-p-phenylenediamine and a particular class of aminohydroxy compounds as alkalizing agent. The aminohydroxy compound is defined as follows:

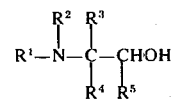

wherein:
a. $R^1$ and $R^2$ are hydrogen, hydroxyethyl or hydroxyisopropyl;
b. $R^3$ and $R^4$ are hydrogen, lower alkyl having 1 to 3 carbons and lower monohydroxyalkyl having 1 to 3 carbons; providing that both $R^3$ and $R^4$ are hydrogen only when either $R^1$ or $R^2$ is hydroxyethyl or hydroxyisopropyl;
c. $R^5$ is hydrogen or methyl.

Examples of suitable aminohydroxy compounds are diethanolamine; triethanolamine; 2-amino-2-methyl-1-propanol; tris(hydroxymethyl)aminomethane; 2-amino-2-methyl-1,3-propanediol; diisopropanolamine; triisopropanolamine.

19 Claims, No Drawings

AQUEOUS ALKALINE HAIR DYE COMPOSITIONS

This is a continuation of application Ser. No. 309,498, filed Nov. 24, 1972, now abandoned.

This invention relates to aqueous hair dye compositions containing $N^1$, $N^4$, $N^4$-tris(2'-hydroxyethyl)-2-nitro-p-phenylenediamine i.e.

(I) 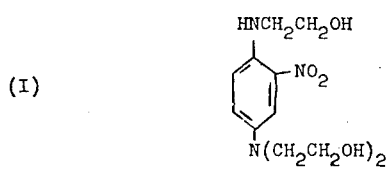

hereinafter referred to as Dye I. More particularly, it concerns hair dye compositions of the aforesaid character suitable for dyeing human hair containing an aminohydroxy compound (hereinafter more particularly defined) as an alkalizing agent.

Dye I has long been used as a blue component in human hair dye compositions of the semi-permanent type. These compositions are direct dye dyeing compositions and are characterized by the fact that they do not require an oxidizing agent to develop the desired color. Moreover, it has been found advantageous to dye these dyes from alkaline solutions.

The use of Dye I was first suggested for use as a direct dyeing hair dye for human hair in the U.S. Pat. No. 2,750,327 to Eckhardt et al. In their dyeing procedure Eckhardt et al recommend the use of a 25% aqueous solution of ammonia as the alkalizing agent. However, in practice the use of aqueous ammonia as the alkalizing agent in compositions containing Dye I had several drawbacks. It was found, for example, that these compositions only gave weak coverage on human hair. As a result, they could not be used to obtain dark shades. Furthermore, the ammonia fumes are irritating to the eyes and nose which is a serious drawback for a product which is intended for use near the face. Consequently, the practice developed of commercially employing monoethanolamine (hereinafter called MEA) as the source of alkali.

The use of MEA as the alkalizing agent in hair dye compositions containing Dye I had proved quite satisfactory from many points of view. However, it was found that the shelf stability of these products left something to be desired. On closer study of this problem, it was discovered that when MEA is used in conjunction with Dye I, a reaction takes place after storage of the composition for 3 months at 50°C or 6 months at 38°C. It has been further found that this dye, which is a blue dye and is ordinarily employed as the blue component in hair dye compositions of this character, was degraded by this reaction and that a yellow dye is produced. This has been confirmed both by thin layer chromatography and by dyeings on human hair. This deleteriously affected the ultimate color of the dyeings obtained on human hair. This yellow dye has been identified as 6-bis(2'-hydroxyethyl)amino-quinoxaline.

It has now been found that the shelf stability of hair dye products containing Dye I may be very materially improved if in place of the MEA, there is employed as alkalizing agent one or more aminohydroxy compounds of formula:

(II) 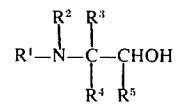

wherein:
a. $R^1$ and $R^2$ are hydrogen, hydroxyethyl or hydroxyisopropyl;
b. $R^3$ and $R^4$ are hydrogen, lower alkyl having 1 to 3 carbons and lower monohydroxyalkyl having 1 to 3 carbons; providing that both $R^3$ and $R^4$ are hydrogen only when either $R^1$ or $R^2$ is hydroxyethyl or hydroxyisopropyl;
c. $R^5$ is hydrogen or methyl. This is an unobvious result in view of the fact that it was previously considered that these materials were essentially the same and no significant effect would be obtained in substituting for MEA these aminohydroxy compounds.

It is, accordingly, an object of this invention to provide a hair dye composition containing Dye I which has greater shelf stability than prior art products containing this dye.

It is also an object of this invention to provide a hair dye composition containing Dye I which employs as alkalizing agent one or more of the aforesaid aminohydroxy compounds.

Other and more detailed objects of this invention will be apparent from the following description and claims.

Brunner et al in their U.S. Pat. No. 3,168,442 suggest that in certain types of direct dyeing hair dye compositions any of a large variety of alkalizing agents may be used to give the hair dye composition an alkaline pH. Among the alkalizing agents enumerated are MEA, DEA and TEA i.e. monoethanol-, diethanol- and triethanolamine respectively. However, Brunner et al make no distinction between these alkalizing agents and in their specific operating examples suggest only the use of the combination of MEA and TEA as the alkalizing system.

The use of TEA or DEA as alkalizing agents in other direct dyeing contexts has also been suggested in the prior art. In this connection, by way of example, attention is directed to U.S. Pat. Nos. 3,119,867; 3,168,441 and 3,634,478. In these references, however, the patentees were not concerned with the use of Dye I nor the storage stability problem encountered with the use of this dye.

Although applicants do not wish to be bound by any theory, in their opinion, the aminohydroxy compounds employed in this invention do not react with Dye I because of the presence of blocking groups in the vicinity of the amino nitrogen of these aminohydroxy compounds. The aminohydroxy compounds employed herein will be one of four general types. They will be either secondary or tertiary amines in which case the 2 or 3 large groups bonded to nitrogen serve as blocking groups for the amine nitrogen. In the third and fourth types of compounds at least one carbon atom adjacent to the amine nitrogen is a secondary or tertiary carbon atom. These also serve as blocking groups to prevent reaction with the amine nitrogen.

Any one or more aminohydroxy compounds falling within formula (II) as described above are useful for the present purposes. To illustrate more particularly the nature of these aminohydroxy compounds, mention may be made of the fact that when $R^3$ and/or $R^4$ are lower alkyl in formula (II) they may be menthyl, ethyl, n-propyl or isopropyl. Moreover, when $R^3$ and/or $R^4$ are lower monohydroxyalkyl, they may be hydroxymethyl, 1-hydroxyethyl

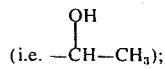

(i.e. $-\overset{\overset{\text{OH}}{|}}{\text{CH}}-\text{CH}_3$);

2-hydroxyethyl (i.e. $-CH_2-CH_2OH$); 1-, 2- or 3-hydroxypropyl; etc. By way of further illustrating the aminohydroxy compounds that are useful herein, mention may be made of diethanolamine (DEA); triethanolamine (TEA); 2-amino-1-butanol (AB); 2-amino-2-methyl-1-propanol (AMP); 2-amino-2-methyl-1,3-propanediol (AMPD); 2-amino-2-ethyl-1,3-propanediol (AEPD); tris (hydroxymethyl) aminomethane (THAM); diisopropanolamine, triisopropanolamine; and mixtures thereof.

The present invention has application to a large variety of aqueous hair dyeing compositions containing Dye I. These may vary from simple aqueous solutions or suspensions of the dye to very sophisticated aqueous compositions such as creams, lotions, pastes, gels, etc. containing blends of other dyes, non-ionic and anionic detergents, solvents, thickeners, perfumes, etc. In these aqueous compositions the carrier of vehicles may be water or a combination of water with other solvents e.g. ethanol. It may also be employed in aerosol emulsion systems in which the dye is contained in an aqueous phase of the system.

The aminohydroxy compound or compounds are employed in this invention to render alkaline the composition from which the dye is to be dyed out. The absolute quantity of these materials incorporated in instant compositions will vary with the nature of the other components in the composition and the final results desired. All that is necessary is that sufficient aminohydroxy compound be added to merely render the composition alkaline. However, in general, it has been found satisfactory to add sufficient amounts of these materials to give the composition a pH in the range of from 7.0 to 11.5. For optimum results the pH should be at a level varying in the range of from 7.5 to 10.5. Where necessary, an acid such as citric acid may be added to bring the pH to the desired level.

As indicated above, the alkalizing agent of this invention may comprise a mixture of aminohydroxy compounds e.g. a combination of DEA and TEA. When a combination of DEA and TEA is employed, the relative quantities of these materials may also vary considerably. However, ordinarily the DEA will comprise between 0.01 to 5.0% by weight of the alkalizing agent, the balance being made of by the TEA.

Surface active agents can also be employed in the dyeing compositions of this invention. These can be anionic, non-ionic or cationic. By way of examples of the various types of surface active agents, there can be mentioned: higher alkylbenzene sulfonates; alkyl-naphthalene-sulfonates; sulfonated esters of alcohols and polybasic acids; taurates; fatty alcohol sulfates; sulfates of branched chain or secondary alcohols; alkyl dimethylbenzyl ammonium chlorides; salts of fatty acids or fatty acid mixtures; N-oxyalkylated fatty acid alkanolamides; and the like. Illustrative of specific surfactants there can be mentioned: sodium lauryl sulfate; polyoxyethylene lauryl ester; myristyl sulfate: glyceryl monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleyl diethanolamide; stearyl dimethyl benzyl ammonium cnloride; dodecyl benzene sodium sulfonate; triethanolamine salt of p-dodecylbenzene sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,0-diethyl tridecanol-6-sulfate and the like. The quantity of surface active agent can vary over a wide range, such as that of from about 0.05% to 15% and preferably from about 0.10% to 5% by weight of the composition.

A thickening agent may also be incorporated in the dyeing composition of this invention which may be one or several of those commonly used in hair dyeing. These are exemplified by such thing as sodium alginate or gum arabic, or cellulose derivatives, such as methylcellulose e.g. Methocel 60HG, or the sodium salt of carboxymethylcellulose, or hydroxyethylcellulose e.g. CELLOSIZE QP-40 or acrylic polymers, such as polyacrylic acid sodium salt, or inorganic thickeners, such as bentonite. The quantity of this thickening agent can also vary over a wide range, such as that of from about 0.1% to 20%, ordinarily it will range from about 0.5% to 5% by weight of the composition.

It is also useful to incorporate an antioxidant in the present dye compositions. A variety of antioxidants are known in the prior art which would be useful for this purpose. Among these mention may be made of the inorganic sulfites, e.g. sodium sulfite, thioglycollic acid and other mercaptans, butylated hydroxy toluene, sodium dithionite, various forms of ascorbic acid and its derivatives e.g. sodium ascorbate, erythrobic acid, ascorbyl palmitate, ascorbyl laurate, etc. The quantity of antioxidant when in use can vary quite a bit. However, this will in general be of the order of about 0.025% to 1% by weight.

Dye I is Incorporated in compositions of this invention in tinctorially effective quantities i.e. in concentrations which are adequate to color the hair. These quantities can vary over a wide range, but ordinarily they will constitute from about 0.001% to greater than about 5% e.g. 10% by weight of the composition. However, preferably, it will comprise from about 0.001% to about 2% by weight of the composition. The major constituent of the composition employed is usually water, and this can vary in amount over a wide range dependent in large measure on the quantity of other additives. Thus, the water content can be as little as 10%, but preferably will amount to from about 70% to 99% by weight of the composition.

The dyeing compositions of this invention are preferably aqueous compositions. The term aqueous composition is used herein in its usual generic sense as embracing any water-containing composition useful for the present purposes. This includes true solutions of the dye in an aqueous medium, either alone or in conjunction with other materials, which are also dissolved or dispersed in the aqueous medium. The term aqueous composition also encompasses any mixture of dye with the aqueous medium either alone or together with other ingredients. The dye may be colloidally dispersed in the medium or may merely be intimately mixed therein. Moreover, the aqueous medium may comprise water or water and an additional or auxilliary solvent. The latter may be employed as a common solvent to enhance the solubility of the dye or some other organic material. Other auxilliary solvents which may be used for this purpose include ethanol, carbitol, isopropanol, propylene glycol, ethylene glycol, glycerine, etc.

Typical dyeing compositions of the simple aqueous alkaline variety described above are set forth below:

1. AQUEOUS ALKALINE COMPOSITIONS

| | General Range | Preferred Range |
| --- | --- | --- |
| Dye I | .001 – 5 % | .001 – 2% |
| Surface active agents | 0.05 – 15% | 0.10 – 5% |
| Alkali | 0.05 – 10% | 0.10 – 5% |
| Thickening agent | 0.1 – 20% | 0.5 – 5% |
| Water | QS to 100% | QS to 100% |
| pH (acid added if necessary) | 7.0 – 11.5 | 7.5 – 10.5 |

Dye I and any of the surface active agents, thickening agents, and combinations thereof set forth above may be used in the proportions specified in the table immediately above. The alkali in these compositions will be any one or more aminohydroxy compounds defined in formula (II) above.

The simple aqueous alkaline dyeing compositions of this invention can be prepared by the conventional methods used in the hair dyeing art. Thus, they can be prepared by dissolving or suspending the dye in water in the desired concentrations. Water miscible organic solvents, e.g. ethanol can be employed to facilitate solution of the dye. In this event, the dye can be dissolved first in the solvent and this solution is then diluted with water. The dispersion of the various ingredients can also be facilitated by heating the composition at temperatures varying from 40°C to 110°C, either before dilution with water or afterwards.

These compositions can be applied to hair by the conventional techniques used in this art. Illustratively, when applied to living hair on the human head, the compositions can be applied to the hair with a brush, sponge, or other means of contact, such as pouring the composition directly onto the hair until saturated. The reaction time or time of contact of the dyeing composition with the hair is not critical and can vary over a wide range used in the hair dyeing art, such as periods of about 5 minutes to about 2 hours. Preferably, a period of from about 5 minutes to about 60 minutes is utilized and most often a period of 10 to 30 minutes. The dyeing temperature can vary over wide limits as is conventional in the art. Thus, the dyeing temperature can vary from about room temperature, e.g. about 20°C to about 60°C, and preferably from about 20°C to about 45°C.

As previously mentioned, the present invention is also applicable to aerosol systems containing an aqueous phase which has incorporated therein Dye I. In this aspect of the invention an aqueous alkaline composition, as described above, is prepared and serves as the aqueous concentrate which is incorporated in the aerosol system. In preparing the aerosol direct dyeing dye composition of this invention, the alkaline concentrate described above (97% to 90% by weight) is mixed with a propellant (3% to 10% by weight). In a preferred form of this aspect of the invention the propellant comprises about 5% by weight of the total aerosol composition, the balance being made up of concentrate.

Any of a variety of propellants well known to those skilled in the art may be used in this aspect of the invention. As used herein, the term propellant means propellant system which may comprise a single propellant component or a combination of propellant components. It is well known in the aerosol art that it is often advantageous to use a mixture of fluorocarbon propellants or the combination of a hydrocarbon propellant and a fluorocarbon propellant to obtain the special benefits which the single component propellants do not exhibit.

In preparing aerosol compositions encompassed in the present invention any of a variety of propellants may be used e.g. gases or low boiling liquids. It may be a fluorinated or a fluorochlorinated lower saturated aliphatic hydrocarbon, and preferably a halogenated alkane containing not more than 2 carbon atoms and at least 1 fluorine atom, or mixtures thereof. The preferred halogenated lower alkane compounds may be represented, generally, by the formula $C_mH_nCl_yF_z$, wherein $m$ is an integer less than 3, $n$ is an integer or zero, $y$ is an integer or zero, and $z$ is an integer, such that $n + y + z = 2_m + 2$. It may also be a liquefied hydrocarbon gas, e.g. butane, isobutane, propane, etc. These may be used alone or admixed with each other. In addition, they may also be employed in admixture with the halogenated propellants mentioned above.

The propellants should preferably possess a boiling point of less than 75°F at 760 mm. pressure. Typical examples of useful propellants are dichlorodifluoromethane ("Freon 12"), dichlorotetrafluoroethane ("Freon 114"), $CClF_2$-$CClF_2$, trichloromonofluoromethane ("Freon 11"), dichloromonofluoromethane ("Freon 21"), monochlorotrifluoromethane ("Freon 13"), $CCl_2$-$CClF_2$ ("Freon 113"), or 1,1-difluoroethane ("Freon 152A").

If it is desired to obtain an aerosol composition which will deliver a cohesive foam with good wetting properties, it is advantageous to use as the propellant blend a mixture of halogenated low molecular weight hydrocarbons at least one of which is a fluorinated hydrocarbon containing no other halogen thereon. Any of a variety of compounds falling within this definition are suitable for the present purposes. However, ordinarily the fluorinated hydrocarbon employed will contain from 1 to 4 carbon atoms and from 2 to 8 fluorine atoms. Moreover, it will usually have a vapor pressure in the range of from about 10 to 115 psia at 70°F. By way of specifically illustrating the fluorinated hydrocarbons that are useful for this purpose, mention may be made of (1,1-difluoroethane) (Freon 152A) and octafluorocyclobutane (Freon C-318). However, in the preferred embodiments of this aspect of the present invention, Freon 152A is employed.

As previously mentioned, propellants systems useful in the present invention to obtain cohesive foams with good wetting properties comprise blends of halogenated low molecular weight hydrocarbons at least one of which is the fluorinated hydrocarbon described above. In addition to the aforesaid fluorinated hydrocarbon, the other component or components of the propellant blend may be any one or more of the well-known halogenated low molecular weight hydrocarbons commonly used as aerosol propellants. These ordinarily will be halogenated hydrocarbons having 1 to 2 carbon atoms and from about 3 to 6 halogenated atoms in which the halogen atoms will ordinarily be chlorine atoms or a mixture of chlorine and fluorine atoms. Moreover, they will usually have a vapor pressure which will fall in the range of from 10 to 115 psia at 70°F.

By way of illustration of the chlorinated or fluorochlorinated propellants that may be employed in this aspect of the invention, mention may be made of Freon 114 ($CClF_2$-$CClF_2$); Freon 12 ($CCl_2F_2$); Freon 11 ($CCl_3F$); Freon 21 ($CHCl_2F$), etc. The relative amounts of fluorinated hydrocarbons which will be contained in the propellant blend employed in this aspect of the present invention may also vary somewhat. Ordinarily, however the fluorinated hydrocarbons will constitute between 20% and 90% by weight of the propellant blend, the balance being made up of one or more chlorinated or fluorochlorinated hydrocarbons.

In preparing the aerosol composition of this invention, the direct dye alkaline concentrate containing Dye I is formulated in the usual manner well known to those skilled in the art and then the desired propellant is added to it. This may be accomplished by either of two methods. One such method involves the so-called "cold filling" wherein the concentrate and propellant are mixed in the cold and then added to the aerosol can which is then capped with an aerosol valve. In another procedure, the direct dye concentrate is charged into a can which is capped with an aerosol valve. The instant propellant blend is then pressure filled through the aerosol valve.

In employing the aerosol compositions of the present invention, in dyeing hair the procedure for use is as follows: shake can well to obtain maximum emulsification or solution of propellant. Hold can so that applicator nozzle is close to the hair. Apply foam and work thoroughly through hair. Allow color to develop on the hair (e.g. 10 to 30 minutes) and then wash excess color solution off the hair.

To test the relative effects on Dye I in storage under regular and under accelerated storage conditions attending the use of aminohydroxy compounds, aqueous solutions were prepared having the following compositions:

TABLE I

| Solution No. | Alkanolamine | Wt. % |
|---|---|---|
| 1 | MEA | 0.8 |
| 2 | DEA | 2.0 |
| 3 | TEA | 3.0 |
| 4 | DEA | 1.0 |
|   | TEA | 1.5 |
| 5 | DEA | 1.3 |
| 6 | TEA | 2.2 |
| 7 | AMP | 1.5 |

TABLE I-continued

| Solution No. | Alkanolamine | Wt. % |
|---|---|---|
| 8 | THAM | 2.5 |
| 9 | AMPD | 1.5 |
| 10 | MIPA | 1.0 |
| 11 | DIPA | 2.0 |
| 12 | TIPA | 3.0 |

All solutions:
Dye I concentration was 0.6 wt. % QS water to 100% pH was 9.70 to 9.75.

The pH's in the above solutions were adjusted with citric acid where necessary to bring the solution to the proper pH. The abbreviations in this table have the following meanings:

Dye I = $N^1,N^4,N^4$-tris(2'-hydroxyethyl)- 2-nitro-p-phenylenediamine
MEA = monoethanolamine
DEA = diethanolamine
TEA = triethanolamine
AMP = 2-amino-2-methyl-1-propanol
THAM = tris(hydroxymethyl)aminomethane
AMPD = 2-amino-2-methyl-1,3-propanediol
MIPA = isopropanolamine
DIPA = diisopropanolamine
TIPA = triisopropanolamine Each of the aforesaid solutions were stored for one week both at room termperature and at 95°C. At the end of this time, the solutions were analyzed spectroscopically and the % of the original dye remaining after storage and the % of yellow dye degradation product produced were determined. These were reported as percentages of the quantity of dye originally present, the original quantity of Dye I being taken as 100%. Thus, a reduction of the amount of Dye I by ½ of the original amount was reported as 50% Dye I. Similarly, an increase of yellow dye which amounts to ½ by weight of the amount of the original quantity of Dye I would be reported as 50% yellow. A summary of the results is given in the Table below:

TABLE II

| Solution | | % Dye I based on Orig. Dye I as 100% | | % Yellow based on Orig. Dye I as 100% | |
|---|---|---|---|---|---|
|   |   | 1 Wk at R.T. | 1 Wk at 95°C | 1 Wk at R.T. | 1 Wk at 95°C |
| 1 | (MEA 0.8%) | 99.8 | 38.3 | Not present | 58.7 |
| 2 | (DEA 2.0%) | 99.8 | 55.6 | " | Not present |
| 3 | (TEA 3.0%) | 100.0 | 68.6 | " | " |
| 4 | (DEA 1.0% & TEA 1.5%) | 100.0 | 59.0 | " | " |
| 5 | (DEA 1.3%) | 100.0 | 54.7 | " | " |
| 6 | (TEA 2.2%) | 100.0 | 64.7 | " | " |
| 7 | (AMP 1.5%) | 100.0 | 74.3 | " | " |
| 8 | (THAM 2.5%) | 100.0 | 79.1 | " | " |
| 9 | (AMPD 1.5%) | 100.0 | 70.3 | " | " |
| 10 | (MIPA 1.0%) | 100.0 | 21.0 | " | 69.0 |
| 11 | (DIPA 2.0%) | 100.0 | 66.3 | " | Not present |
| 12 | (TIPA 3.0%) | 100.0 | 79.6 | " | " |

As shown in Table II, both MEA and MIPA react with Dye I after one week at 95°C to form a yellow dye, 6-bis(2'-hydroxyethyl)amino-quinoxaline. In the process, Dye I undergoes extensive decomposition. In the case of the aminohydroxy compounds employed in this invention, no yellow dye is formed after one week at 95°C, and also Dye I suffers less decomposition.

To further test the effect on the dyeing characteristics of dye compositions containing Dye I and having incorporated therein DEA as compared with MEA as the alkalizing agent after regular storage and under accelerated storage conditions, two dye formulas were prepared containing 0.6% by weight of Dye I. Each of these formulas was identical in all respects excepting that Dye Formula A contained 0.9% MEA whereas Dye Formula B contained 2.0% DEA. Since DEA is a weaker base than MEA, it was necessary to use a larger quantity of the former to bring Dye Formula B up to the same pH as Dye Formula A i.e. pH 9.6. These formulas contained the typical components ordinarily found in hair dye compositions e.g. surfactants, solvents, thickening agents, antioxidants, etc. Samples of each of the aforesaid Dye Formulas A and B were stored for 1 week both at room temperature and at 95°C. Fresh samples of these dye formulas, as well as the aforesaid stored samples of the dye formulas, were each used to dye human hair employing the following procedure:

Grey human hair was saturated with the above lotion dye formulas which is at room termperature and placed in a 38°C oven for 20 minutes. After the 20 minutes, the samples were removed from the oven and rinsed in lukewarm water until the water runs clean. Then the hair is dried and evaluated.

The results of these dyeing experiments are summarized in the Table below:

TABLE III

MEA Dye Formula A

| | |
|---|---|
| Original | Violet |
| 1 Week storage at room temperature | Violet equal to original in depth and shade |
| 1 Week storage at 95°C | Light Ash Brown due to large loss of violet and the formation of the yellow |

DEA Dye Formula B

| | |
|---|---|
| Original | Violet |
| 1 Week storage at room temperature | Violet equal to original in depth and shade |
| 1 Week storage at 95°C | Dull violet due to loss of violet about 35% |

The following Examples are given to further illustrate the present invention. It is to be understood, however, that the invention is not limited thereto. Unless otherwise specified, percentages are given in percent by weight.

EXAMPLE 1

| Ingredients | Per Cent |
|---|---|
| $N^1,N^4,N^4$-tris(2'-hydroxyethyl)-2-nitro-p-phenylenediamine | 0.600 |
| Diethanolamine | 2.000 |
| Carbitol | 4.000 |
| Lauric Diethanolamide | 1.500 |
| Triethanolamine Linear Alkylate Sulfonate | 0.500 |
| Polyoxyethylene Hydrogenated Fatty Amide | 1.900 |
| Sodium Carboxymethyl Cellulose | 2.400 |

EXAMPLE 1-continued

| Ingredients | Per Cent |
|---|---|
| Oleic Acid | 1.000 |
| Perfume | 0.125 |
| Water q.s. | 100.000 |
| pH | 9.600 |

EXAMPLE 2

| Ingredients | % by Wt. |
|---|---|
| $N^1,N^4,N^4$-tris(2'-hydroxyethyl)-2-nitro-p-phenylenediamine | 0.60 |
| Diethanolamine | 2.00 |
| Carbitol | 4.00 |
| Lauric Diethanolamide | 1.50 |
| Triethanolamine Salt of p-dodecylbenzenesulfonate | 0.50 |
| $CH_3(CH_2)_7CH=CH(CH_2)_7CON[CH_2CH_2O)_{25}H]_2$ | 1.90 |
| *Methylcellulose | 2.40 |
| Oleic Acid | 1.00 |
| Perfume | 0.125 |
| Water q.s. | 100.00 |
| pH | 9.6 |

*Methylcellulose referred to herein and elsewhere is characterized as follows: methoxyl content 27.5 to 31.5%; viscosity of 2% aqueous solution at 20°C in Centipoise 1500; average M.W. 63,000.

Examples 3 and 4 following are given in tabular form. The formula of Example 3 is a gel and will give a light pearl shade on human grey hair. The formula of Example 4 is a cream and will give a medium pearl shade on human grey hair.

| Ingredients | Ex. 3 Gel | Ex. 4 Cream |
|---|---|---|
| $N^1,N^4,N^4$-tris(2'-hydroxyethyl)-2-nitro-p-phenylenediamine | 0.030% | 0.060% |
| TEA | — | 0.800% |
| DEA | 2.750% | — |
| Carbitol | 5.000% | 3.500% |
| Lauric Diethanolamide | 3.000% | 1.800% |
| Polyoxyethylene Hydrogenated Fatty Amide | 1.800% | 1.500% |
| Na-Carboxymethyl Cellulose | 4.200% | 2.800% |
| Oleic Acid | 1.500% | 2.000% |
| Perfume | 0.100% | 0.125% |
| Water q.s. | 100.000% | 100.000% |
| pH | 9.8 | 8.0 |

The ingredients listed in the following Examples are mixed to give an oil-in-water emulsion in which the dyes are contained in the oil phase. A slurry is formed by mixing the Carbitol with the dyes. To this is then added the lauric diethanolamide. These materials are stirred to form a homogeneous mixture. To this is then added the ethoxylated fatty amide, oleic acid and diethanolamine as the batter is stirred. The batter is then brought to 50% dilution with water, and the methyl cellulose is added and the mixture is stirred an additional 1 hour. After this, the water is added to bring the composition up to 100%. Final shade obtained with this composition will be medium brown.

| Ingredients | % by weight of concentrate | | | | | |
|---|---|---|---|---|---|---|
| | Ex.5 | Ex.6 | Ex.7 | Ex.8 | Ex.9 | Ex.10 |
| Carbitol | — | 4 | 4 | — | 4 | — |
| Oleic Acid | 2 | — | 2 | — | — | 2 |
| Lauric diethanolamide | 1.5 | 1.5 | 1.5 | 1.5 | 1.5 | 1.5 |
| $CH_3(CH_2)_7-CH=CH(CH_2)_7CON[(CH_2CH_2O)_{25}H]_2$ | 1.5 | 1.5 | — | 1.5 | — | — |
| DEA | 0.8 | 0.8 | 0.8 | 0.8 | 0.8 | 0.8 |

-continued

| Ingredients | % by weight of concentrate | | | | | |
|---|---|---|---|---|---|---|
| | Ex.5 | Ex.6 | Ex.7 | Ex.8 | Ex.9 | Ex.10 |
| Methyl cellulose | 1.2 | 1.2 | 1.2 | 1.2 | 1.2 | 1.2 |
| $N^1,N^4,N^4$-tris(2-hydroxyethyl)2-nitro-p-phenylenediamine | 0.5 | 0.5 | 0.5 | 0.5 | 0.5 | 0.5 |
| 1,4,5,8-tetraaminoanthraquinone | 0.15 | 0.15 | 0.15 | 0.15 | 0.15 | 0.15 |
| 4-Nitro-o-phenylenediamine | 0.08 | 0.08 | 0.08 | 0.08 | 0.08 | 0.08 |
| 2-Nitro-p-phenylenediamine | 0.05 | 0.05 | 0.05 | 0.05 | 0.05 | 0.05 |
| Water | QS 100 | QS 100 | QS 100 | QS 100 | QS 100 | QS 100 |

Each of the aforesaid concentrates i.e. concentrates of Examples 5 to 10 are employed in preparing three types of aerosol compositions which contain 95% by weight of concentrate and 5% by weight of propellant blend. In one type of aerosol composition the propellant blend consists of 65% by weight of Freon 152A and 35% by weight of Freon 114 based on the total weight of propellant blend. In another type of aerosol composition the propellant blend consists of 35% by weight of Freon 12, 30% by weight of Freon 152A and 35% by weight of Freon 114 based on the total weight of the propellant blend. In a third type of aerosol composition the propellant blend consists of 15% by weight of Freon 12, 50% by weight of Freon 152A and 35% by weight of Freon 114. These compositions will give medium brown shades.

The two following Examples are also given in tabular form. Concentrates are prepared having the compositions set out in Examples 11 and 12 below and were used to prepare aerosol compositions. Ninety-five percent (95%) by weight of each of these concentrates were mixed with 5% by weight of a propellant blend having the following composition:

| | | |
|---|---|---|
| Freon 12 ($CCl_2F_2$) | | 35% by wt. |
| Freon 152A (1,1-difluoroethane) | | 30% by wt. |
| Freon 114 ($CClF_2$-$CClF_2$) | | 35% by wt. |
| Ingredients | Ex.11 | Ex.12 |
| $N^1,N^4,N^4$-tris(2'-hydroxyethyl)-2-nitro-p-phenylenediamine | 0.5 | 0.5 |
| 1,4,5,8-tetraaminoanthraquinone | 0.15 | 0.15 |
| 4-nitro-o-phenylenediamine | 0.12 | 0.08 |
| 2-nitro-p-phenylenediamine | 0.05 | 0.03 |
| 2(2-ethoxyethoxy)ethanol | 4.0 | 5.0 |
| Lauric diethanolamide | 1.5 | — |
| Linoleic monoethanolamide | 1.5 | 2.5 |
| $CH_3(CH_2)_7CH=CH(CH_2)_7CON[(CH_2CH_2O)_{25}H]_2$ | 1.5 | — |
| Ethoxylated (75 E.O.) lanolin alcohols | 1.5 | — |
| Ethoxylated (15 E.O.) rosin fatty acids | — | 3.0 |
| Oleic Acid | 2.0 | — |
| Tallow Fatty Acids | — | 2.0 |
| DEA | 0.8 | 0.8 |
| Methylcellulose | 2.4 | — |
| Fumed Silica | — | 2.4 |
| Water | q.s. to 100% | q.s. to 100% |

Although the invention has been described with reference to specific forms thereof, it will be understood that many changes and modifications may be made without departing from the spirit of this invention.

What is claimed is:

1. An aqueous alkaline hair dyeing composition comprising an aqueous alkaline medium containing therein a tinctorial quantity of $N^1,N^4,N^4$-tris(2'-hydroxyethyl)-2-nitro-p-phenylenediamine and an alkalizing agent in an amount sufficient to render the composition alkaline, said alkalizing agent being an aminohydroxy compound selected from the group consisting of diethanolamine; triethanolamine; 2-amino-2-methyl-1-propanol; tris(hydroxymethyl)aminomethane; 2-amino-2-methyl-1,3-propanediol; diisopropanolamine; triisopropanolamine and a mixture of diethanolamine and triethanolamine.

2. The composition according to claim 1 having a pH in the range of from about 7.0 to 11.5.

3. The composition according to claim 1 containing 0.001 to 5.000% by weight based on the total weight of the aqueous composition of $N^1$, $N^4,N^4$-tris(2'-hydroxyethyl)-2-nitro-p-phenylenediamine.

4. The composition according to claim 1 wherein said alkalizing agent is diethanolamine.

5. The composition according to claim 1 wherein said alkalizing agent is triethanolamine.

6. The composition according to claim 1 wherein said alkalizing agent is a combination of diethanolamine and triethanolamine.

7. The composition according to claim 1 wherein said alkalizing agent is 2-amino-2-methyl-1-propanol.

8. The composition according to claim 1 wherein said alkalizing agent is tris(hydroxymethyl)aminomethane.

9. The composition according to claim 1 wherein said alkalizing agent is 2-amino-2-methyl-1,3-propanediol.

10. The composition according to claim 1 wherein said alkalizing agent is diisopropanolamine.

11. The composition according to claim 1 wherein said alkalizing agent is triisopropanolamine.

12. The composition according to claim 1 wherein said aqueous alkaline composition comprises the aqueous phase of an aerosol composition, said aerosol composition also comprising a propellant system.

13. The composition according to claim 1 in the form of an aqueous solution.

14. The composition according to claim 1 in which the aqueous compositions comprise the aqueous phase of an emulsion.

15. The composition according to claim 1 in the form of an aqueous lotion.

16. The composition according to claim 1 in the form of an aqueous cream.

17. The composition according to claim 1 in the form of an aqueous paste.

18. The composition according to claim 1 in the form of an aqueous gel.

19. An aqueous alkaline hair dyeing composition comprising an aqueous alkaline medium containing therein tinctorial quantity of $N^1,N^4,N^4$-tris(2'-hydroxyethyl)-2-nitro-p-phenylenediamine and an alkalizing agent, said alkalizing agent being an aminohydroxy compound selected from the group consisting of diethanolamine; triethanolamine; 2-amino-2-methyl-1-propanol; tris(hydroxymethyl)aminomethane; 2-amino-2-methyl-1,3-propanediol; diisopropanolamine; triisopropanolamine and a mixture of diethanolamine and triethanolamine; said aqueous alkaline hair dyeing composition having a pH in the range of from about 9.70 to 9.75.

* * * * *